United States Patent [19]

Cordi et al.

[11] Patent Number: 5,208,260
[45] Date of Patent: May 4, 1993

[54] VINYL GLYCINE DERIVATIVES FOR MEMORY AND LEARNING ENHANCEMENT OR TREATMENT OF A COGNITIVE DISORDER

[75] Inventors: Alex A. Cordi, St. Louis; Joseph B. Monahan, Black Jack, both of Mo.; Robert M. Williams, Fort Collins, Colo.

[73] Assignee: G. D. Searle & Co., Chicago, Ill.

[21] Appl. No.: 501,640

[22] Filed: Mar. 29, 1990

[51] Int. Cl.$^5$ .................... A01N 37/12; A01N 37/44
[52] U.S. Cl. .................................................... 514/561
[58] Field of Search ........................................ 514/561

[56] References Cited

U.S. PATENT DOCUMENTS

| | | | |
|---|---|---|---|
| 4,837,219 | 6/1989 | Hutterer | 514/561 X |
| 4,871,550 | 10/1989 | Millman | 514/561 X |
| 4,994,492 | 2/1991 | Kendall et al. | 514/561 |
| 5,028,622 | 7/1991 | Plaitakis | 514/561 |

Primary Examiner—Paul F. Shaver
Attorney, Agent, or Firm—Charles E. Smith; J. Timothy Keane; Paul D. Matukaitis

[57] ABSTRACT

A class of vinyl glycine derivatives is described for use in memory and learning enhancement or for treatment of a cognitive disorder. The vinyl glycine derivatives of particular interest are compounds of Formula I wherein the double bond is in trans configuration, $R^1$ is lower alkyl, $R^2$ is hydrido, $R^3$ is amino and X is hydroxymethyl.

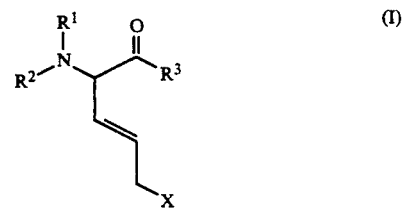

5 Claims, No Drawings

VINYL GLYCINE DERIVATIVES FOR MEMORY AND LEARNING ENHANCEMENT OR TREATMENT OF A COGNITIVE DISORDER

FIELD OF THE INVENTION

This invention is in the field of clinical neurology and relates specifically to compounds, formulations and methods for memory enhancement and for treatment of cognitive disorders.

BACKGROUND OF THE INVENTION

There are many memory-related conditions for which therapeutic treatments are under investigation, such as methods to enhance memory or to treat memory dysfunction. Memory dysfunction is believed to be linked to the aging process, as well as to neurodegenerative diseases such as Alzheimer's disease. Also, memory impairment can follow head trauma or multi-infarct dementia. Many compounds and treatments have been investigated which can enhance cognitive processes, that is, which can improve memory and retention.

The compound piracetam has been prescribed for treatment to enhance memory [Giurgea et al, *Arch. Int. Pharmacodyn. Ther.*, 166, 238 (1967)]. U.S. Pat. No. 4,639,468 to Roncucci et al describes the compound milacemide which is mentioned as useful for treatment of memory troubles. Further investigations of milacemide have documented the memory-enhancing capabilities of milacemide in human subjects [B. Saletu et al, *Arch. Gerontol. Geriatr.*, 5, 165-181 (1986)].

The effects of milacemide on memory have been correlated with the increase in brain glycine content which follows milacemide administration. This specific glycine effect is suspected to be mediated through the recently discovered strychnine-insensitive glycine receptor (also known as the "Glycine B" receptor site) [J. B. Monahan et al., *J. Neurochemistry*, 53, 370-375 (1989)]. So far the structure-activity relationships developed around this receptor have shown that the highest affinities are obtained with small, hydrophilic amino acids of the D-isomer configuration such as D-serine and D-alanine [L. D. Snell et al., *Eur. J. Pharmacol.*, 156, 105-110 (1988)] and aminocyclopropyl carboxylic acid ["ACC"; V. Nadler et al., *Eur. J. Pharmacol.*, 157, 115-116 (1988)].

Certain vinyl glycine derivatives have been reported as antibiotics and enzyme inhibitors. For example, the inhibition of bacterial methionine-γ-lyase by L-2-amino-3-trans-pentenoate has been reported [M. Johnson et al., *Biochemistry*, 20, 4325-4333 (1981)]. Also, the compound L-2-amino-4-methoxy-trans-3-butenoic acid, isolated from *Pseudomonas aeruginosa*, has been shown to be an irreversible inhibitor of the L-aspartate aminotransferase enzyme [R. R. Rando, Nature, 250, 587-588 (1974)].

DESCRIPTION OF THE INVENTION

Improvement of cognitive function or treatment of a cognitive dysfunction is achieved by treatment of a subject with a therapeutically-effective amount of a vinyl glycine derivative or a prodrug thereof. Such vinyl glycine derivative or prodrug thereof may be provided by one or more compounds selected from a family of compounds defined by Formula I:

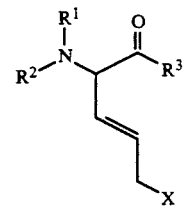

wherein $R^1$ is selected from hydrido, alkyl, haloalkyl, alkoxyalkyl, cycloalkyl, aralkyl and aryl; wherein $R^2$ is selected from hydrido, alkyl, aralkyl, aryl,

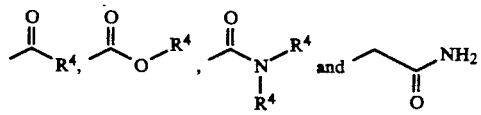

wherein $R^1$ and $R^2$ may be taken together to form a Schiff-base derived group selected from derivatives of aldehydes and ketones; wherein $R^3$ is selected from $OR^4$, $NR^4H$ and

with $R^4$ selected from hydrido, alkyl, haloalkyl, alkoxyalkyl, cycloalkyl, aralkyl and aryl; and wherein X is selected from hydrido, alkyl, hydroxyalkyl, acyloxyalkyl and trialkylsilyloxyalkyl; or a pharmaceutically-acceptable salt thereof.

The compounds embraced by Formula I with the above-described substituents are believed to be novel when the following proviso description is incorporated into Formula I, that is, when $R^3$ is $OR^4$ and $R^4$ is selected from hydrido and alkyl, then $R^1$ and $R^2$ cannot be selected from hydrido, methyl, ethyl, n-propyl, isopropyl, n-butyl, sec-butyl isobutyl, tert-butyl and benzyl.

The phrase "improvement of cognitive function or treatment of a cognitive dysfunction" embraces treatment to improve or enhance memory and treatment to address a cognitive deficit linked to a neurological disorder.

A preferred family of compounds of Formula I consists of compounds wherein $R^1$ is selected from hydrido, lower alkyl, haloalkyl, cycloalkyl, alkoxyalkyl, phenalkyl and phenyl; wherein $R^2$ is selected from hydrido, lower alkyl, phenalkyl, phenyl,

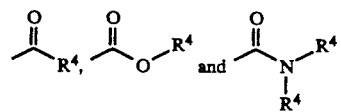

wherein the Schiff-base derived group is derived from acetylacetone, salicylaldehyde, benzophenone derivatives and acetylacetic acid esters; wherein $R^3$ is selected from hydroxy, $OR^4$, $NH_2$ and $NHR^4$; wherein $R^4$ is selected from alkyl, haloalkyl, aralkyl and aryl; and wherein X is selected from hydrido, alkyl, hydroxyalkyl and acetoxyalkyl.

A more preferred group of compounds within Formula I consists of these compounds wherein $R^1$ is selected from hydrido, lower alkyl and phenalkyl; wherein $R^2$ is selected from hydrido,

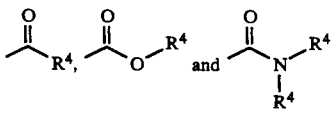

wherein the Schiff-base derived group is selected from

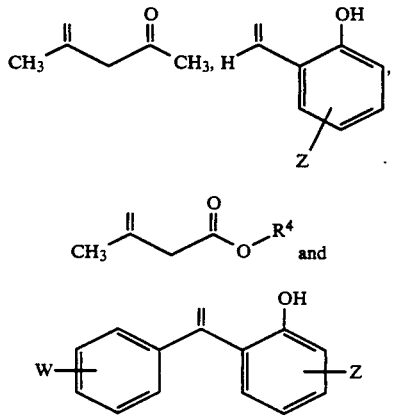

wherein each of Z and W is independently one or more groups selected from lower alkyl and halo; wherein $R^3$ is selected from hydroxy, $OR^4$ and $NH_2$; wherein $R^4$ is selected from alkyl and aryl; and wherein X is selected from hydrido, alkyl, hydroxyalkyl and acetoxyalkyl.

A particularly preferred group of compounds of Formula I consists of those compounds wherein the double bond is trans in configuration, the stereochemistry of the amino acid is in the D configuration, $R^1$ is selected from lower alkyl and phenalkyl; $R^2$ is hydrido; $R^3$ is selected from $OR^4$ and amino, with $R^4$ selected from alkyl and aryl; and X is hydroxymethyl or acetoxymethyl.

A most preferred group of compounds within Formula I consists of those compounds wherein $R^1$ and $R^2$ are taken together to form a Schiff-base derived group selected from

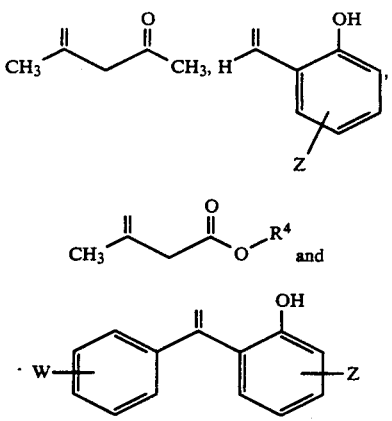

wherein each of Z and W is independently one or more groups selected from fluoro, chloro and bromo; wherein $R^3$ is selected from amino and $OR^4$, wherein $R^4$ is selected from alkyl and aryl; and wherein X is selected from hydrido, alkyl, hydroxyalkyl and acetoxyalkyl.

A class of compounds of particular interest consists of those compounds of Formula I wherein $R^1$ is lower alkyl; $R^2$ is hydrido, $R^3$ is amino and X is hydroxymethyl.

The term "hydrido" denotes a single hydrogen atom (H) which may be attached, for example, to a carbon atom to form a hydrocarbyl group or attached to an oxygen atom to form a hydroxy group. Where the term "alkyl" is used, either alone or within another term such as "haloalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about ten ring carbon atoms, preferably three to about five carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkoxy" and "alkoxyalkyl" embrace linear or branched oxy-containing radicals having alkyl portions of one to about ten carbon atoms, such as methoxy and methoxymethyl, respectively. The term "aralkyl" is exemplified by "phenalkyl" of which benzyl is a specific example.

Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl.

Included within the family of compounds of Formula I are the isomeric forms of the described compounds including diastereoisomers, stereoisomers of the double bond (cis and trans or Z and E), enantiomers (D and L or R and S) and the pharmaceutically-acceptable salts thereof. The term "pharmaceutically-acceptable salts" embraces salts commonly used to form alkali metal salts and to form addition salts of free acids or free bases. Since the compounds of Formula I contain basic nitrogen atoms, such salts are typically acid addition salts or quaternary salts. The nature of the salt is not critical, provided that it is pharmaceutically acceptable. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by reacting, for example, the appropriate acid or base with the corresponding compound of Formula I.

The term "prodrug", as used herein, embraces compounds which are precursors of the vinyl glycine derivatives of Formula I. Such precursor compounds can release the vinyl glycine derivative by some chemical or enzymatic reaction taking place in the body or, optimally, in the brain.

Various methods have been specifically developed for the synthesis of vinyl glycine amino acids. R. G. Shea et al. described the synthesis of this class of compounds by the transposition of allylic selenides [*J. Org. Chem.*, 51, 5243–5252 (1986)]. F. Heinzer and D. Bellus reported on a general method of synthesis of vinyl glycine derivatives through oxazoline intermediates [*Helv. Chim. Acta*, 64, 2279–2297 (1981)]. W. Greenlee was able to sort out the conditions leading to increased yields in the Strecker reaction of α,β-unsaturated aldehydes [*J. Org. Chem.*, 49, 2632–2634 (1984)]. This method is particularly amenable to the synthesis of N-substituted vinyl glycine derivatives such as, for example, 2-benzylamino-3-trans-pentenoic acid and 2-isopropylamino-3-trans-heptenoic acid. Another method was developed by J. S. Edler et al. who through the use of a phosphonium salt synthon, was able to synthesize a large array of vinyl glycine derivatives and, particularly, ethyl 2-amino-3-trans-hexenoate [*Tetrahedron Letters*, 29, 3361–3364 (1988)].

Compounds of Formula I can be synthesized from these aforementioned amino acid precursors by several different methods. For example, starting from N-acyl derivatives of the vinyl glycines described by R. M. Williams and Weixu Zhai [*Tetrahedron*, 44, 5425–5430 (1988)], the carboxylic functions of these N-protected forms of vinyl glycine amino-acids may be activated either by reaction with a diimide such as diclyclohexyldiimide (DCC) in for instance, dichloromethane, or by the mixed anhydride method and reacted with an alcohol or amine to give the desired ester or amide of the invention (Scheme I). In Scheme I, Y represents a good leaving group such as a halogen atom, an acyl group, carbamoyl group or an azido group, useful to activate the carboxylic function.

Scheme I:

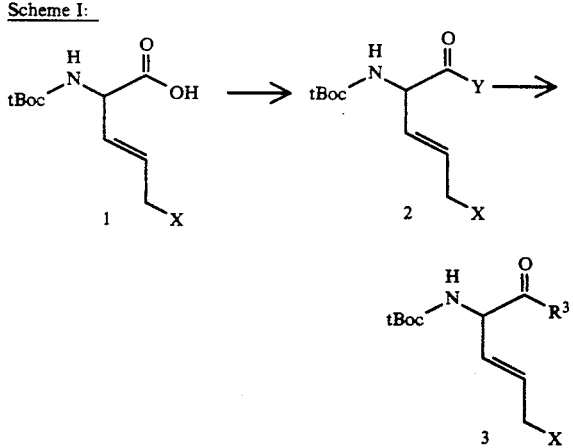

The protecting group may then be removed, usually in the presence of an acid such as trifluoroacetic acid, and the transformation of the amino function carried out. For instance, the compound 4 may be reacted with an acyl chloride in the presence of a base such as pyridine, triethylamine, sodium hydroxide, or potassium hydroxide, in a protic or aprotic solvent, such as water, chloroform, dichloromethane, ether or toluene, to yield acyl derivatives of 5 (Scheme II).

Scheme II:

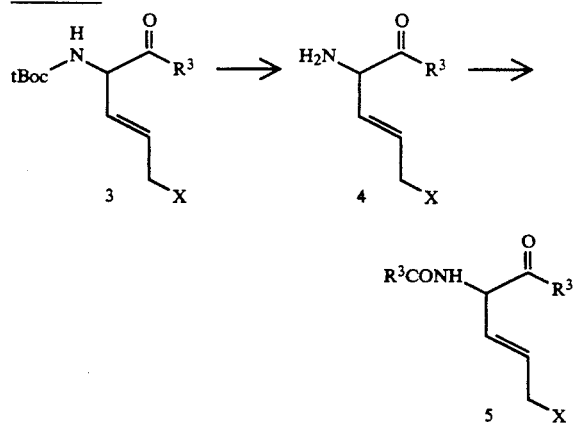

Intermediate 4 can also be alkylated by reacting it with any $R^1$—Y (where $R^1$ and Y have the values previously defined) in the presence of a base, preferentially an organic base, such as pyridine or triethylamine, or an inorganic base, such as sodium hydroxide or potassium carbonate, in the presence of a phase-transfer catalyst, in a solvent or mixture of solvents able to dissolve the reactants and coreactants, and at a temperature between room temperature and the reflux temperature of the selected solvent or mixture thereof (Scheme III).

Scheme III:

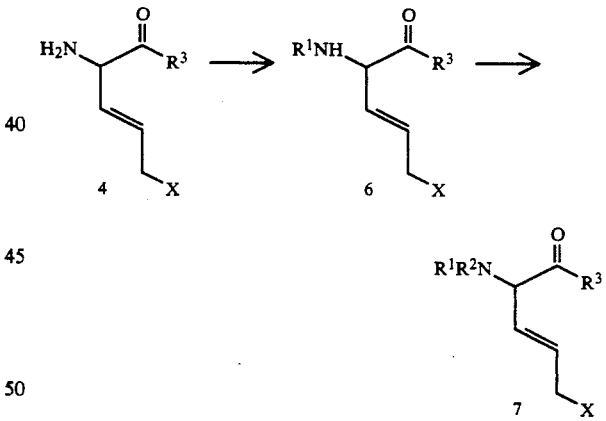

Another method to synthesize the derivatives of compound 6 is to treat 4 with an aldehyde $R^5COH$ or a ketone $R^5R^6CO$ [where $R^5$ and $R^6$ have such values that $R^5CH_2$— and $R^5R^6CH$— are equivalent to $R^1$ and $R^2$, respectively] in a reducing atmosphere provided by, for instance, hydrogen in the presence of a noble metal catalyst (palladium, platinum, nickel) or a boron or aluminum hydride, such as sodium borohydride, or preferentially sodium or lithium cyanoborohydride. These two alkylating methods could be used in combination to produce compound 7. Either a two step process can be performed where two different alkylating agents are introduced consecutively, or a large excess of the alkylating reagent can be used to obtain compounds 7 where $R^1 = R^2$. The intermediate amine 4 could also be reacted with an aldehyde or a ketone to form an imine 8. The best yields are obtained when the water formed during the reaction is removed from the reaction mixture. This can be achieved either by conducting the reaction in a solvent, such as an alcohol, or in a chlorinated or aromatic solvent, such as ethanol, methanol, toluene, benzene, dichloromethane or chloroform, in the presence of molecular sieves, or through azeotropic distillation with a Dean-Stark trap (Scheme IV).

Scheme IV:

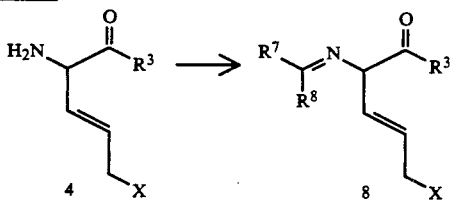

wherein $R^7$ and $R^8$ taken together are the Schiff-base imine residues described previously for Formula I.

Stereospecific synthesis of the D- and L-amino-acids as well as the D,L-mixture may be obtained by the method of Scheme V and are part of the invention. Synthesis of the cis double bond isomer may be obtained by reducing the acetylenic intermediate 9 by a poisoned noble metal catalyst such as the Lindlar catalyst or Pd in the presence of quinoline.

Scheme V:

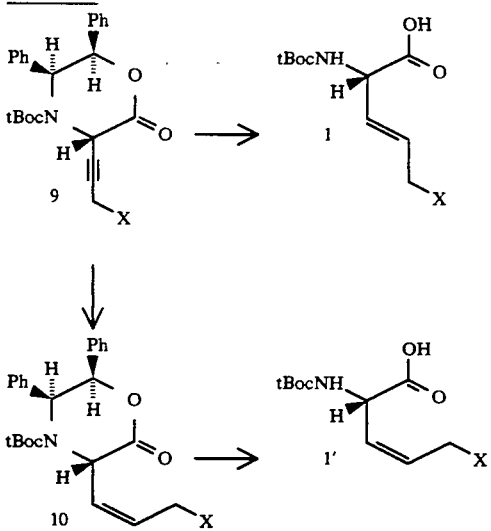

Examples of compounds of the invention which can be prepared by the methods just described are the following:

trans-L-2-amino-pent-3-enoic acid;
trans-D-2-amino-pent-3-enoic acid;
trans-L-2-amino-hept-3-enoic acid;
trans-D-2-amino-hept-3-enoic acid;
trans-L-2-amino-dec-3-enoic acid;
trans-D-2-amino-dec-3-enoic acid;
trans-D-2-amino--6-hydroxy-hex-3-enoic acid;
trans-L-2-amino-6-hydroxy-hex-3-enoic acid;
trans-D-2-amino-6-trimethylsilyloxy-hex-3-enoic acid;
trans-L-2-amino-6-trimethylsilyloxy-hex-3-enoic acid;
trans-D-2-amino-6-acetoxy-hex-3-enoic acid;
trans-L-2-amino-6-acetoxy-hex-3-enoic acid;
trans-D-2-amino-6-benzoyloxy-hex-3-enoic acid;
trans-L-2-amino-6-benzoyloxy-hex-3-enoic acid;
trans-D-2-amino-6-pivaloyloxy-hex-3-enoic acid;
trans-L-2-amino-6-pivaloyloxy-hex-3-enoic acid;
trans-D-2-n,pentylamino-6-hydroxy-hex-3-enoic acid;
trans-L-2-n,pentylamino-6-hydroxy-hex-3-enoic acid;
trans-D-2-n,pentylamino-6-trimethylsilyloxy-hex-3-enoic acid;
trans-L-2-n,pentylamino-6-trimethylsilyloxy-hex-3-enoic acid;
trans-D-2-n,pentylamino-6-acetoxy-hex-3-enoic acid;
trans-L-2-n,pentylamino-6-acetoxy-hex-3-enoic acid;
trans-D-2-n,pentylamino-6-benzoyloxy-hex-3-enoic acid;
trans-L-2-n,pentylamino-6-benzoyloxy-hex-3-enoic acid;
trans-D-2-n,pentylamino-6-pivaloyloxy-hex-3-enoic acid;
trans-L-2-n,pentylamino-6-pivaloyloxy-hex-3-enoic acid;
trans-D-2-n,pentylamino-6-hydroxy-hex-3-enoic amide;
trans-L-2-n,pentylamino-6-hydroxy-hex-3-enoic amide;
trans-D-2-n,pentylamino-6-trimethylsilyloxy-hex-3-enoic amide;
trans-L-2-n,pentylamino-6-trimethylsilyloxy-hex-3-enoic amide;
trans-D-2-n,pentylamino-6-acetoxy-hex-3-enoic amide;
trans-L-2-n,pentylamino-6-acetoxy-hex-3-enoic amide;
trans-D-2-n,pentylamino-6-benzoyloxy-hex-3-enoic amide;
trans-L-2-n,pentylamino-6-benzoyloxy-hex-3-enoic amide;
trans-D-2-n,pentylamino-6-pivaloyloxy-hex-3-enoic amide;
trans-L-2-n,pentylamino-6-pivaloyloxy-hex-3-enoic amide;
trans-L-2-amino-pent-3-enoic ethyl ester;
trans-D-2-amino-pent-e-enoic n,propyl ester;
trans-L-2-amino-hept-3-enoic methyl ester;
trans-D-2-amino-hept-3-enoic t,butyl ester;
trans-L-2-amino-dec-3-enoic i,propyl ester;
trans-D-2-amino-dec-3-enoic i,butyl ester;
trans-D-2-amino 6-hydroxy-hex-3-enoic ethyl ester;
trans-L-2-amino-6-hydroxy-hex-3-enoic n,octyl ester;
trans-L-2-amino-pent-3-enoic ethyl ester;
trans-D-2-acetamido-pent-3-enoic n,propyl ester;
trans-L-2-formamido-hept-3-enoic methyl ester;
trans-D-2-benzamido-hept-3-enoic t,butyl ester;
trans-L-2-valeramido-dec-3-enoic i,propyl ester;
trans-D-2-trifluoroacetamido-dec-3-enoic i,butyl ester;
trans-D-2-pivalamido-6-hydroxy-hex-3-enoic ethyl ester;
trans-L-2-salicilamido-6-hydroxy-hex-3-enoic n,octyl ester;
trans-L-2-amino-pent-3-enoic acid, acetophenone imine;
trans-D-2-amino-pent-3-enoic acid, benzophenone imine;
trans-L-2-amino-hept-3-enoic acid, acetylacetone imine;
trans-D-2-amino-hept-3-enoic acid, ethyl acetylacetate imine;
trans-L-2-amino-dec-3-enoic acid, butylphenylketone imine;
trans-D-2-amino-dec-3-enoic acid, o,hydroxybenzophenone imine;
trans-D-2-amino-6-hydroxy-hex-3-enoic acid, o,hydroxy-p,chlorobenzophenone imine;
trans-L-2-amino-6-hydroxy-hex-3-enoic acid, o,hydroxy-m,fluorobenzophenone imine;

trans-L-2-amino-pent-3-enoic amide, acetophenone imine;
trans-D-2-amino-pent-3-enoic amide, benzophenone imine;
trans-L-2-amino-hept-3-enoic amide, acetylacetone imine;
trans-D-2-amino-hept-3-enoic amide, ethyl acetylacetate imine;
trans-L-2-amino-dec-3-enoic amide, butylphenylketone imine;
trans-D-2-amino-dec-3-enoic amide, o,hydroxybenzophenone imine;
trans-D-2-amino-6-hydroxy-hex-3-enoic amide, o,hydroxy-p,chlorobenzophenone imine;
trans-l-2-amino-6-hydroxy-hex-3-enoic amide, o,hydroxy-m,fluorobenzophenone imine;
cis-L-2-amino-pent-3-enoic acid;
cis-D-2-amino-pent-3-enoic acid;
cis-L-2-amino-hept-3-enoic acid;
cis-D-2-amino-hept-3-enoic acid;
cis-L-2-amino-dec-3-enoic acid;
cis-D-2-amino-dec-3-enoic acid;
cis-D-2-amino-6-hydroxy-hex-3-enoic acid;
cis-L-2-amino-6-hydroxy-hex-3-enoic acid;
cis-D-2-amino-6-trimethylsilyoxy-hex-3-enoic acid;
cis-L-2-amino-6-trimethylsilyloxy-hex-3-enoic acid;
cis-D-2-amino-6-acetoxy-hex-3-enoic acid;
cis-L-2-amino-6-acetoxy-hex-3-enoic acid;
cis-D-2-amino-6-benzoyloxy-hex-3-enoic acid;
cis-L-2-amino-6-benzoyloxy-hex-3-enoic acid;
cis-D-2-amino-6-pivaloyloxy-hex-3-enoic acid;
cis-L-2-amino-6-pivaloyloxy-hex-3-enoic acid;
cis-D-2-n,pentylamino-6-hydroxy-hex-3-enoic acid;
cis-L-2-n,pentylamino-6-hydroxy-hex-3-enoic acid;
cis-D-2-n,pentylamino-6-trimethylsilyloxy-hex-3-enoic acid;
cis-L-2-n,pentylamino-6-trimethylsilyloxy-hex-3-enoic acid;
cis-D-2-n,pentylamino-6-acetoxy-hex-3-enoic acid;
cis-L-2-n,pentylamino-6-acetoxy-hex-3-enoic acid;
cis-D-2-n,pentylamino-6-benzoyloxy-hex-3-enoic acid;
cis-L-2-n,pentylamino-6-benzoyloxy-hex-3-enoic acid;
cis-D-2-n,pentylamino-6-pivaloyloxy-hex-3-enoic acid;
cis-L-2-n,pentylamino-6-pivaloyloxy-hex-3-enoic acid;
cis-D-2-n,pentylamino-6-hydroxy-hex-3-enoic amide;
cis-L-2-n,pentylamino-6-hydroxy-hex-3-enoic amide;
cis-D-2-n,pentylamino-6-trimethylsilyloxy-hex-3-enoic amide;
cis-L-2-n,pentylamino-6-trimethylsilyloxy-hex-3-enoic amide;
cis-D-2-n,pentylamino-6-acetoxy-hex-3-enoic amide;
cis-L-2-n,pentylamino-6-acetoxy-hex-3-enoic amide;
cis-D-2-n,pentylamino-6-benzoyloxy-hex-3-enoic amide;
cis-L-2-n,pentylamino-6-benzoyloxy-hex-3-enoic amide;
cis-D-2-n,pentylamino-6-pivaloyloxy-hex-3-enoic amide;
cis-L-2-n,pentylamino-6-pivaloyloxy-hex-3-enoic amide;
cis-L-2-amino-pent-3-enoic ethyl ester;
cis-D-2-amino-pent-e-enoic n,propyl ester;
cis-L-2-amino-hept-3-enoic methyl ester;
cis-D-2-amino-hept-3-enoic t,butyl ester;
cis-L-2-amino-dec-3-enoic i,propyl ester;
cis-D-2-amino-dec-3-enoic i,butyl ester;
cis-D-2-amino 6-hydroxy-hex-3-enoic ethyl ester;
cis-L-2-amino-6-hydroxy-hex-3-enoic n,octyl ester;
cis-L-2-amino-pent-3-enoic ethyl ester;
cis-D-2-acetamido-pent-3-enoic n,propyl ester;
cis-L-2-formamido-hept-3-enoic methyl ester;
cis-D-2-benzamido-hept-3-enoic t,butyl ester;
cis-L-2-valeramido-dec-3-enoic i,propyl ester;
cis-D-2-trifluoroacetamido-dec-3-enoic i,butyl ester;
cis-D-2-pivalamido-6-hydroxy-hex-3-enoic ethyl ester;
cis-L-2-salicilamido-6-hydroxy-hex-3-enoic n,octyl ester;
cis-L-2-amino-pent-3-enoic acid, acetophenone imine;
cis-D-2-amino-pent-3-enoic acid, benzophenone imine;
cis-L-2-amino-hept-3-enoic acid, acetylacetone imine;
cis-D-2-amino-hept-3-enoic acid, ethyl acetylacetate imine;
cis-L-2-amino-dec-3-enoic acid, butylphenylketone imine;
cis-D-2-amino-dec-3-enoic acid, o,hydroxybenzophenone imine;
cis-D-2-amino-6-hydroxy-hex-3-enoic acid, o,hydroxy-p,chlorobenzophenone imine;
cis-L-2-amino-6-hydroxy-hex-3-enoic acid, o,hydroxy-m,fluorobenzophenone imine;
cis-L-2-amino-pent-3-enoic amide, acetophenone imine;
cis-D-2-amino-pent-3-enoic amide, benzophenone imine;
cis-L-2-amino-hept-3-enoic amide, acetylacetone imine;
cis-D-2-amino-hept-3-enoic amide, ethyl acetylacetate imine;
cis-L-2-amino-dec-3-enoic amide, butylphenylketone imine;
cis-D-2-amino-dec-3-enoic amide, o,hydroxybenzophenone imine;
cis-D-2-amino-6-hydroxy-hex-3-enoic amide, o,hydroxy-p,chlorobenzophenone imine; and
cis-L-2-amino-6-hydroxy-hex-3-enoic amide, o,hydroxy-m,fluorobenzophenone imine.

Of particular interest are compounds which have been selected for biological evaluation as identified below in Table I:

TABLE I

| Compound # | Formal Name |
| --- | --- |
| 1 | trans-L-2-amino-pent-3-enoic acid |
| 2 | trans-D-2-amino-pent-3-enoic acid |
| 3 | trans-L-2-amino-hept-3-enoic acid |
| 4 | trans-D-2-amino-hept-3-enoic acid |
| 5 | trans-L-2-amino-dec-3-enoic acid |
| 6 | trans-D-2-amino-dec-3-enoic acid |
| 7 | trans-D-2-amino-6-hydroxy-hex-3-enoic acid |
| 8 | trans-L-2-amino-6-hydroxy-hex-3-enoic acid |

Another group of compounds of particular interest are the amide derivatives of the specific acid compounds listed in Table 1. These amide derivatives are preferred inasmuch as such amide compounds would likely be more bioavailable in the brain than the acid counterpart compounds and thus would be expected to be more therapeutically beneficial.

BIOLOGICAL EVALUATION

[$^3$H]Glycine binding was performed using Triton X-100 washed synaptic plasma membranes (SPM) prepared from rat forebrain (30–45 day old, male Sprague Dawley; Sasco, St. Charles Mo.). The assay was initiated by the addition of 0.2–0.4 mg of SPM to an incubation containing 10 nM [$^3$H]glycine (43.5 Ci/mmole; New England Nuclear, Boston Mass.), and various concentrations of the appropriate test compounds in a total volume of 1 ml, with all additions made in 50 nM Tris/acetate, pH 7.4. Following a 10 min incubation at 2° C. the bound radioactivity was separated from the free by either centrifugation (12000 g for 25 min at 4° C.) or vacuum filtration through Whatman GF/B filters using a Brandel MB-18 Harvester. The $K_d$ and $B_{max}$ values for [$^3$H]glycine were similar using either separation technique. The radioactivity associated with the SPM was quantitated using liquid scintillation spectrometry. $K_i$ values for the inhibition of [$^3$H]glycine binding were determined using logit-log analysis, with nonspecific binding determined using 100 $\mu$M glycine. Modulation of [$^3$H]TCP binding was performed using Triton X-100 (0.04% v/v) treated rat SPM that had been extensively washed. Assay incubations were at 25° C. for 60 min and contained 5.0 nM [$^3$H]TCP, and various concentrations of the test compound in 5 mM Tris/HCl, pH 7.4. The assay was stopped by rapid filtration, using a Brandel MB-48 Harvester, thru Whatman GF/B filters treated with 0.05% polyethylenimine and the samples washed four times with 2.0 mls cold buffer. Radioactivity associated with the filter was determined by liquid scintillation spectrometry as described above. Nonspecific binding was defined using 60 $\mu$M PCP. Results are shown in Table II.

TABLE II

| COMPOUND # | STRUCTURE | AFFINITY [$^3$H]GLYCINE ($K_i$, $\mu$M) | AG/ANTAG [$^3$H]TCP | |
|---|---|---|---|---|
| | | | CONC ($\mu$) | % STIM* |
| 1 | | 7.2 | 40 | 51 |
| 2 | | 4.8 | ND | ND |
| 3 | | 4.9 | 12 | 66 |
| 4 | | 1.8 | ND | ND |
| 5 | | 0.95 | 30 | 78 |
| 6 | | 55.0 | 100 | 48 |
| 7 | | 0.28 | 6 | 67 |
| 8 | | 0.77 | ND | ND |

*The stimulation of [$^3$H]TCP binding (% STIM) was expressed as a percentage of the maximal glycine stimulation observed in the assay. The stimulation of [$^3$H]TCP binding is indicative of agonist character, while inhibition of [$^3$H]TCP binding is indicative of antagonist character.
ND = not determined.

Based on the data in Table II obtained from the previously-described functional analysis assay, the vinyl glycine derivatives of this invention, which are examples of large lipophilic amino-acids, interact at the glycine modulatory site exhibiting agonist characteristics. These results are evidence for involvement of the Glycine receptor in modulation of the NMDA receptor and thus vinyl glycine derivatives would be valuable tools to probe NMDA receptor function. More importantly, Glycine B agonists would be expected to provide therapeutic benefits in treatment of cognitive dysfunctions, such as Alzheimer's Disease, age-associated memory impairment, multi-infarct dementia, mixed organic brain syndrome, metabolic encephalopathies of various origins, alcoholic dementia and various learning disorders. In particular, the Glycine B agonist compounds would be useful in treatment of Alzheimer's Disease, age-associated memory impairment and learning deficit, in human subjects suffering from such disorders, as well as for use in improvement of memory and learning ability in healthy individuals.

The acidic amino acids, aspartic and glutamic acid, have been found to possess both excitatory and excitotoxic properties [J. W. Olney, Science, 164, 719–721 (1969); J. W. Olney et al., Exp. Brain Res., 14, 61–76 (1971)]. Indeed, neurons which have excitatory amino acid receptors on their dendritic or somal surfaces undergo acute excitotoxic degeneration when these receptors are excessively activated by glutamic acid.

Glycine agonists which have a modulating effect on the NMDA transmission would be expected to increase the glutamic acid transmission and achieve beneficial excitatory effects without the detrimental excitotoxic side effect. Most glycine ligands are very polar molecules and hardly cross the blood brain barrier. Because of the difficulty in crossing the blood brain barrier, such ligands are not bioavailable at concentrations effective to be therapeutically beneficial.

It was surprising and unexpected that these large and lipophylic vinyl glycine derivatives were found to have such a good affinity for the strychnine-insensitive Glycine receptor as shown by the binding data above. Glycine agonists are believed to facilitate NMDA transmission and, therefore, to have a positive effect on memory Long Term Potentiation (LTP). The improvement in LTP is linked to memory enhancement.

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 0.2 mg to about 50 mg per kilogram of body weight. Most preferred is a dosage in a range from about 0.3 to about 25 mg per kilogram of body weight per day. A suitable dose can be administered in multiple sub-doses per day. These sub-doses may be administered in unit dosage forms. Typically, a dose or sub-dose may contain from about 1 mg to about 1000 mg of active compound per unit dosage form. A more preferred dosage will contain from about 2 mg to about 500 mg of active compound per unit dosage form. Most preferred is a dosage form containing from about 3 mg to about 250 mg of active compound per unit dose.

The active compound is usually administered in a pharmaceutically-acceptable formulation. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain a controlled-release formulation as may be provided in a disposition of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to improve cognitive function or to treat cognitive dysfunction by administering to a subject a therapeutically-effective amount of a vinyl glycine derivative or a prodrug thereof, selected from compounds and their pharmaceutically-acceptable salts, of the group consisting of
trans-L-2-amino-pent-3-enoic acid;
trans-D-2-amino-pent-3-enoic acid;
trans-L-2-amino-hept-3-enoic acid;
trans-D-2-amino-hept-3-enoic acid;
trans-L-2-amino-dec-3-enoic acid;
trans-D-2-amino-dec-3-enoic acid;
trans-D-2-amino-6-hydroxy-hex-3-enoic acid; and
trans-L-2-amino-6-hydroxy-hex-3-enoic acid.

2. The method of claim 1 wherein said vinyl glycine derivative is trans-L-2-amino-dec-3-enoic acid or a pharmaceutically-acceptable salt thereof.

3. The method of claim 1 further characterized by administering said vinyl glycine derivative or prodrug thereof to a subject for treating age-associated memory impairment.

4. The method of claim 1 further characterized by administering said vinyl glycine derivative or prodrug thereof for treating a learning deficit.

5. The method of claim 1 further characterized by administering said vinyl glycine derivative or prodrug thereof for improving memory or learning ability.

* * * * *